United States Patent
Metz

Patent Number: 5,853,006
Date of Patent: Dec. 29, 1998

[54] PRESERVATIVE

[76] Inventor: Joachim Metz, Am Bauenhaus 57, DE-40472 Dusseldorf, Germany

[21] Appl. No.: 426,156

[22] Filed: Apr. 21, 1995

[30] Foreign Application Priority Data

Apr. 21, 1994 [DE] Germany .......................... 44 13 879.2
Feb. 17, 1995 [DE] Germany ......................... 195 05 378.8

[51] Int. Cl.⁶ .................................................. A61F 6/04
[52] U.S. Cl. ........................................ 128/844; 128/918
[58] Field of Search .................................. 128/842, 844, 128/918; 604/347–353

[56] References Cited

U.S. PATENT DOCUMENTS

| | | | |
|---|---|---|---|
| 2,567,926 | 9/1951 | Dunkelberger | 128/844 |
| 2,670,736 | 3/1954 | Dunkelberger . | |
| 3,282,414 | 11/1966 | Penksa | 128/844 |
| 4,872,463 | 10/1989 | Nishizono | 128/844 |
| 5,070,890 | 12/1991 | Papurt . | |
| 5,163,448 | 11/1992 | Foldesy . | |
| 5,163,449 | 11/1992 | van der Valk | 128/844 |
| 5,234,401 | 8/1993 | Yamanaka . | |
| 5,267,575 | 12/1993 | Hrishko | 128/842 |
| 5,479,940 | 1/1996 | Babled | 128/844 |
| 5,549,120 | 8/1996 | Persson | 128/844 |

FOREIGN PATENT DOCUMENTS

| | | |
|---|---|---|
| A-2693652 | 1/1994 | France . |
| 2695029 | 3/1994 | France . |
| C-199408 | 6/1908 | Germany . |
| C-232797 | 3/1911 | Germany . |
| 867582 | 2/1953 | Germany . |
| 1566302 | 4/1970 | Germany . |
| 37 30 911 A1 | 3/1989 | Germany . |
| 41 30 220 | 3/1994 | Germany . |
| 184721 | 8/1936 | Switzerland . |
| 490848 | 8/1970 | Switzerland . |
| 2253352 | 9/1992 | United Kingdom . |
| 225335219 | 9/1992 | United Kingdom . |
| WO 88/02624 | 4/1988 | WIPO . |
| WO 93/17645 | 9/1993 | WIPO . |
| WO 94/10945 | 5/1994 | WIPO . |

OTHER PUBLICATIONS

European Search Report dated Oct. 23, 1995.

Primary Examiner—Michael A. Brown
Attorney, Agent, or Firm—Alix, Yale & Ristas, LLP

[57] ABSTRACT

A preservative comprises a conventional condom rolled about an applicator ring defining member(s) comprised of resilient material. The ring may be formed by cutting an elongated elastic member to length and elastically deforming the member into an annular shape. Alternatively, the ring may be composed of a plurality of C-shaped ring sectors. In either case, the ring will fall off the condom upon the latter being unrolled.

11 Claims, 1 Drawing Sheet

PRESERVATIVE

BACKGROUND OF THE INVENTION

1. Field of the Invention

The present invention relates to devices generally characterized as preservatives, i.e., protective appliances which may prevent the spread of disease, and particularly to condoms. More specifically, this invention is directed to facilitating the application of, and thus encouraging the use of, condoms. Accordingly, the general objects of the present invention are to provide novel and improved devices and methods of such character.

2. Description of the Prior Art

Conventionally, condoms are sold in a rolled shape. When the condom is to be applied, it must be unrolled which requires a certain manual aptitude. Hence, existing condoms are not without problems in use.

Regardless of the manner in which it was packaged, the characteristics of a condom, particularly its flexibility, may degrade in storage. Accordingly, it is not rare that a condom will fail during application unless the user spends all his attention to the manipulation which sometimes results in a premature loss of penile erection.

For the foregoing reason, some individuals refuse to use condoms. Venereal and acquired immune deficiency disease risks, however, require that the use of condoms should be accepted. Accordingly, there has been a longstanding desire to render such use as uncomplicated as possible.

Prior art proposals intended to simplify the use of condoms were only partly successful. For example, British Patent 2 253 352 discloses a preservative comprising an annular applicator provided with a groove for receiving a rolled condom. The elastomeric condom is intended to be applied by means of the applicator but unrolls relative to the applicator with friction so that the condom may be damaged. The annular applicator of the preservative of British Patent 2 253 352 has a weakened portion because, other than the condom itself, the preservative is not expandable. As the preservative in use must engage the penis with elastic bias, but is non-biased when housed in a package, the proper dimensioning of the applicator appears to be problematic.

A further similar prior art preservative is disclosed in Patent Cooperation Treaty publication WO 88/02624. In this example of the prior art, the open end of the condom is biased to an increased diameter by means of the applicator.

U.S. Pat. No. 5,163,448 discloses a preservative wherein the condom is rolled on a thicker ring made of elastic material in an attempt to facilitate handling. The ring is deformable and shaped as a closed loop. Accordingly, after application of the condom, the ring must be rolled back.

A further rolled preservative provided with an annular ring is shown in U.S. Pat. No. 3,282,414. The device of this patent has a hollow ring which surrounds the condom roll torus and houses a fluid which is delivered upon unrolling while the condom rolls relative to the annular ring. The annular ring is cut so that it may be easily removed once a securing web is torn off.

SUMMARY OF THE INVENTION

It is an object of the present invention to provide a preservative which is easy to apply.

It is a further object of the invention to provide a preservative having a condom which may be applied with little attention of the user, even in the dark.

It is another object of the invention to provide a condom including means to facilitate its application but, once applied, does not differ from conventional condoms.

It is also an object of the invention to provide a preservative having the advantages mentioned above but whose fabrication does not significantly increase its costs.

The preservative of the present invention comprises a conventional condom rolled on a thickening ring to facilitate its manipulation. The ring is radially cut at least once and formed by bending a piece of resilient material into annular form prior to its being rolled into the condom. In result, upon termination of the application of the condom, the ring or its parts freely fall off, as a result of a return toward their original unbent shape, and no manipulation is required for ring removal.

In a first embodiment, a predetermined length of an elongated resilient material, e.g., a foam rubber string, is elastically bent into annular shape at the machine provided for rolling the condoms after their being tested, and the condom is rolled about this "applicator" to provide the preservative ready for application. Once the condom is unrolled, the ring-forming material comes free and assumes its previous elongated shape.

In an alternative embodiment, the annular shaped applicator may be made up of a plurality of sectors, e.g., two or three.

If the applicator ring has only two sectors, these sectors should be elastically deformed, from substantially straight pieces, prior to rolling. If there are three or more sectors, they may be formed as such without necessity to deform them upon rolling of the condom because, upon unrolling, they lose engagement with the condom and fall off.

BRIEF DESCRIPTION OF THE DRAWINGS

These and other objects and advantages of the invention will be described below with reference to the accompany drawings, in which.

DESCRIPTION OF THE DISCLOSED EMBODIMENTS

Figure 2:
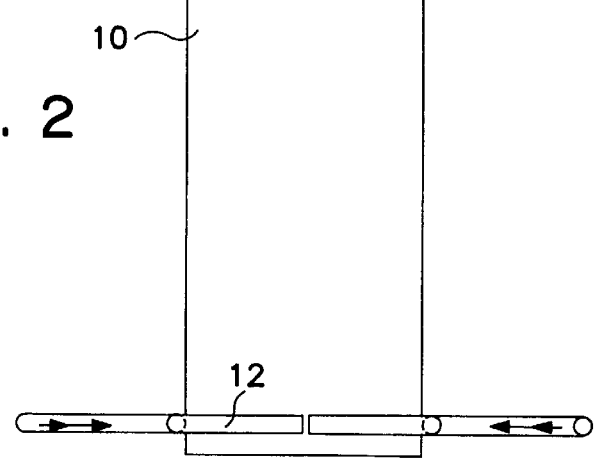
FIG. 2 shows an unrolled preservative according to a first embodiment of the invention.
Figure 1:
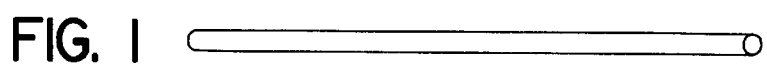
FIG. 1 illustrates an elongated piece of resilient material to be deformed into an annular shape to function as the applicator of a preservative in accordance with the invention.

Referring first to FIG. 2, a condom is indicated at 10 and shown in unrolled condition. When condom 10 was rolled to form a preservative in accordance with the invention, it had a much thicker roll torus than ordinary condoms because of the applicator ring 12. Accordingly, a preservative in accordance with the invention is characterized by facilitating handling and manipulation. FIG. 1 shows the elongated piece of resilient material from which ring 12 is formed after its production and prior to its deformation into an annular shape. For example, the piece 12 may be cut to length from a foam rubber string. Alternatively, ring 12 may be formed from an inflatable, thin-walled member. Prior to rolling condom 10 about piece 12, the ends of the latter are bent towards one another and, preferably, brought into abutting relation, cf. FIG. 3. Bending is indicated by the arrows in FIG. 2. Once the condom is unrolled, because of its elasticity, piece 12 assumes its original "straight" shape so as to come free of condom 10.

It will be understood that the terms "elongated" and "straight", as used herein, do not necessarily means "straight"; the piece must just be "straight enough" to fall off without requiring any manipulation. For example, ring 12' (FIG. 4) is composed of three "elongated", i.e., substantially C-shaped sectors which, of course, also fall off once the condom is applied. For sake of clarity, the gap 14 between the three sectors is illustrated with an exaggerated width in FIG. 4.

Figure 4:
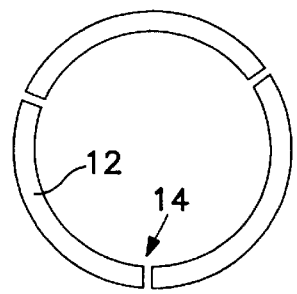
FIG. 4 is a top plan view of an alternative applicator comprising a plurality of sectors.
Figure 3:
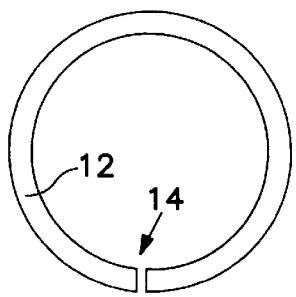
FIG. 3 is a top plan view of the resilient material of FIG. 1 bent into annular shape.

In both of the embodiments of FIGS. 3 and 4, the ring elements may, as noted above, be thin-walled tubular members filled or inflated with air, such tubular members being particularly deformable upon rolling and unrolling.

Figure 5:
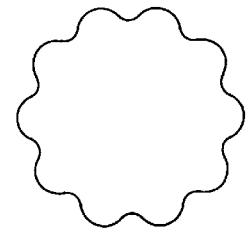
FIGS. 5 and 6 schematically represent third and fourth alternative applicator structures in accordance with the invention.
Figure 6:
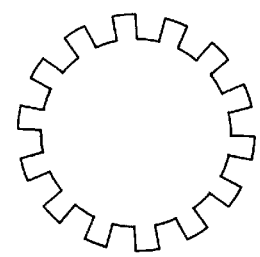

The undulated application ring contour represented in FIG. 5 or the notched ring contour of FIG. 6 facilitate rolling of the preservative into the marketable shape during fabrication. It will be understood that the preservative, after being rolled, will be placed in a sterile package.

To facilitate manufacture, the deformed applicator ring 12 of FIG. 3 or the ring sectors of FIG. 4 may be temporarily bonded to the condom by means of a suitable adhesive, the adhesive being selected such that it loses its bonding force after a short time to permit the ring or ring elements to fall away from the condom.

It may also be advisable to provide, at the condom opening, an outwardly flared lip engaging beneath the ring element or elements thereby further facilitating rolling of the condom about the ring.

The condom of the invention should be coated with a friction-reducing material at least on portions which are exposed prior to application. Such friction-reducing material facilitates further the unrolling operation when the preservative is used.

While a preferred embodiment of the foregoing invention has been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. A preservative comprising a condom and applicator means, said applicator means defining a thickened, discontinuous ring, said applicator means being formed from a substantially straight member comprised of a resilient material which has been elastically bent to assume a generally annular shape, said condom being rolled about said applicator means to form a bead which accommodates said applicator means.

2. The preservative of claim 1 wherein said member is divided into a plurality of arcuate ring sector elements brought into said generally annular shape by having their ends abutting one another.

3. The preservative of claim 1 wherein said resilient material is a polymeric material.

4. The preservative of claim 1 wherein said member comprises an inflated thin-walled tubular element.

5. The preservative of claim 1 wherein said applicator means defined ring has a notched contour.

6. The preservative of claim 1 wherein at least those portions of the condom which are exposed are coated an anti-friction material.

7. A preservative comprising a condom and applicator means, said applicator means being formed of resilient material and defining a thickened, discontinuous ring comprising a plurality of arcuate ring sector elements, said elements being brought into generally annular form by having their ends abutting one another, at least one of said ring sector elements comprising an inflated thin-walled tubular element, said condom being rolled about said applicator means to form a bead which accommodates said applicator means.

8. A preservative comprising a condom and applicator means, said applicator means defining a thickened, discontinuous ring having an undulating contour, said applicator means being formed of a resilient material, said condom being rolled about said applicator means to form a bead which accommodates said applicator means.

9. The preservative of claim 8 wherein said ring is comprised of at least three separate ring sectors.

10. A preservative comprising a condom and applicator means, said applicator means defining a thickened, discontinuous ring comprised of at least three separate ring sectors, said applicator means sectors being formed of a resilient material, said condom being rolled about said applicator means to form a bead which accommodates said applicator means, said condom being temporarily adhesively bonded to said applicator means ring sectors.

11. The preservative of claim 10 wherein said applicator means ring sectors comprise thin-walled tubular members.

* * * * *